(12) United States Patent
Chang et al.

(10) Patent No.: US 7,465,455 B2
(45) Date of Patent: Dec. 16, 2008

(54) FUSION PROTEIN OF PORCINE REPRODUCTIVE AND RESPIRATORY SYNDROME VIRUS AS PRRS VACCINE

(75) Inventors: Hsiu-Kang Chang, Taipei (TW); Chao-Wei Liao, Shin-Chu (TW)

(73) Assignee: Healthbanks Biotech Co., Ltd., Taipei (TW)

( * ) Notice: Subject to any disclaimer, the term of this patent is extended or adjusted under 35 U.S.C. 154(b) by 286 days.

(21) Appl. No.: 11/480,387

(22) Filed: Jul. 5, 2006

(65) Prior Publication Data

US 2008/0008722 A1 Jan. 10, 2008

(51) Int. Cl.
*A61K 39/12* (2006.01)
(52) U.S. Cl. ........................................ 424/204.1; 435/6
(58) Field of Classification Search .............. 424/204.1; 435/6
See application file for complete search history.

(56) References Cited

U.S. PATENT DOCUMENTS

2004/0247617 A1 12/2004 Liao et al. ................ 424/192.1

2008/0019912 A1* 1/2008 Harris et al. ................. 424/9.2

OTHER PUBLICATIONS

Ansari et al. Journal of Virology, Apr. 2006, vol. 80, No. 8, pp. 3994-4004.*
Eric J. Snijder et al., "Heterodimerization of the Two Major Envelope Proteins Is Essential for Arterivirus Infectivity", Journal of Virology, Jan. 2003, p. 97-104.
M:. Ostrowski et al., "Identification of Neutralizing and Nonneutralizing Epitopes in the Porcine Reproductive and Respiratory Syndrome Virus GP5 Ectodomain", Journal of Virology, May 2002, p. 4241-4250.

* cited by examiner

*Primary Examiner*—Ali R. Salimi
(74) *Attorney, Agent, or Firm*—Intellectual Property Connections, Inc.; Hsin-Ming Saunders

(57) ABSTRACT

A fusion protein of porcine reproductive and respiratory syndrome virus (PRRSV) for PRRSV vaccine. The fusion protein includes: (a) a Pseudomoitas Exoloxin A (PE) peptide that comprises a binding domain and a translocating domain; (b) a peptide fragment that contains a N-terminal portion of PRRSV ORF6 protein; (c) a peptide fragment that has a N-terminal portion of PRRSV ORF5 protein; and (d) a carboxyl terminal domain that comprises an amino acid seciuence KDEL. The PE peptide is located at the N-terminus of the fusion protein, and the peptide fraament containinC the N-terminal portion of PRRSV ORF5 protein is located between the peptide fragment containing the N-terminal portion of PRRSV ORF6 protein and the carboxyl terminal domain.

20 Claims, 6 Drawing Sheets

FUSION PROTEIN OF PORCINE REPRODUCTIVE AND RESPIRATORY SYNDROME VIRUS AS PRRS VACCINE

BACKGROUND OF THE INVENTION

1. Field of the Invention

The present invention relates to a fusion protein of PRRS subunit vaccine inducing PRRSV neutralization titers in pigs.

2. Description of Related Art

Porcine reproductive and respiratory syndrome is a porcine infectious disease that primarily strikes respiratory tracts of pigs at various ages and results in sows having reproductive dysfunction. PRRSV is a tough and resistant virus not prone to evoke antibodies having neutralization titers in the infectious pig. Besides, PRRSV is a RNA virus and reproduces easily on the basis of a simplified genetic system, so the probability of genetic mutations is very high. Furthermore, infections and pathogenesis pathway of PRRS virus can be sorted into two stages: (A) infections of epithelium tissues of upper and lower reproductive tracts; and (B) infections of monocytes and macrophages in tissues surrounding reproductive tracts. Thus, the host must have body fluid immunity as well as mucosal immunity with neutralization titers and also a cell-mediated immune response to facilitate removal of the infected viruses and strengthen the host protection mechanisms. However, it is not very easy for PRRSV infectious pig to have neutralization titers in natural conditions, hence typical antibodies basically have little effect on PRRSV, and they even induce mutations in viruses. Furthermore, in antibody-dependent enhancement of phagocytosis, the antibodies could only cause more severe PRRSV infections.

Taiwan Patent No.1-2289933 (also as U.S. patent publication no. 2004/02147617) discloses a target-cell-specific fusion protein, which utilizes a moiety and a functional domain of *Pseudomonas aeruginosa* exotoxin to fuse a PRRSV ORF7 nuclear protein fragment, with a KDEL signal peptide added on the carboxyl terminus. The fusion protein can be mass-produced in *E. coli*. When immunized the fusion protein to pigs, it is possible to decrease or to eliminate viremia after being PRRSV-challenged in the immunized pigs. The full text of the patent is incorporated herein.

In heterodimerization between ORF5 and ORF6 of PRRSV, epitope Cys-34 of ORF5 and epitope Cys-8 of ORF6 play a critical role in viral infection and the envelope assembly thereof. (Snijder Eric J., Jessica C. et al., Journal of Virology, January 2003, Vol. 77, No. 1:97-104). Besides, the consensus sequence of PRRSV ORF5 (YKNTHLDLIYNA) is an epitope between amino acid $38^{th}$ and amino acid $44^{th}$, which is located at N-terminal extracellular domain of PRRSV ORF5 and had been identified as a neutralization epitope (Ostrowski M., J. A. Galeota, et al., Journal of Virology, May 2002, Vol. 76, No. 9:4241-4250).

Prior arts disclose constructing whole PRRSV ORF5 or ORF6 antigens between PE and KDEL. After immunization of these fusion proteins, the pigs suffered from severe inflammation in their lungs post being PRRSV-challenged, indicating that PRRSV ORF5 or ORF6 have an antigen-specific allergy effect. Manifestly, it is difficult to use them as PRRS vaccine antigens. Thus, to develop a vaccine and effectively protect pigs from PRRS infections, there are a lot of difficulties that have to be overcome. It should need to be designed such as a lower immunotoxicity and having a high neutralization titer.

SUMMARY OF THE INVENTION

An object of the present invention is to provide a fusion protein, and the method to construct thereof.

Anther object of the present invention relates to using the fusion protein to prepare a subunit vaccine composed of proteins having neutralization titers.

Still another object of the present invention is to provide a pharmaceutical composition, comprising the fusion protein of the present invention and pharmaceutically acceptable adjuvants.

PE-PQGAB-K3 fusion protein of the present invention comprises: a chimeric polypeptide containing N-terminal portions of PRRSV ORF5 and ORF6 structure proteins; a portion of *Pseudomonas exotoxin* A binding and translocation domains; and a carboxyl terminal domain containing fragment.

The present invention further comprises a pharmaceutical composition that can serve as a vaccine, comprising: a chimeric polypeptide, which contains N-terminal portions of PRRSV ORF5 and ORF6 structural proteins; a portion of *Pseudomonas exotoxin* A binding and translocation domain; a carboxyl terminal domain containing fragment; and a pharmaceutically acceptable adjuvant.

The strain of PRRSV in the present invention is not particularly limited. It can be an American strain, European strain, or Australian strain. There is no particular limitation to the fragments contained in the N-terminal domain of the fusion protein, but they are preferably any PRRSV fragment that is antigenic, such as PRRSV ORF5, ORF6. Taking the American strain as an example, the portion of PRRSV ORF6 sequence is preferably as SEQ ID NO.13. The amino acid sequence of the N-terminal portion of PRRSV ORF5 structural protein can be as SEQ ID NO.12. For the European strain, the amino acid sequence of the N-terminal portion of PRRSV ORF6 structural protein is preferably as SEQ ID NO.14, and that of the N-terminal portion of PRRSV ORF5 can be as SEQ ID NO.15.

In the present invention, the nucleic acid sequence of the fusion protein containing a portion of PRRSV ORF5 and a portion of PRRSV ORF6 is modified, and there is no particular limitation to the sequence, but it is preferably a nucleic acid sequence that can be expressed in large amounts in *E. coli* host-vector system, and the expressed proteins are identical to wild type ones. Taking the American strain of PRRSV as an example, preferably the modified nucleic acid sequence is as seen in SEQ ID NO.1. For the European strain, preferably the modified nucleic sequence is as SEQ ID NO.11.

A preferred embodiment of the portion of *Pseudomonas exotoxin* A binding and translocation domain of the fusion protein in the present invention is a detoxified *Pseudomonas exotoxin*, which is a fragment from *Pseudomonas exotoxin* A without domain III. Preferably, the fragment of *Pseudomonas exotoxin* A binding and translocation domain acts as a ligand moiety which is capable of reacting, recognizing or binding to a receptor on the target cell.

The pharmaceutical composition of the present invention can comprise a suitable adjuvant known in the art: dispersant, humectant (such as Tween 80), or sterile injections prepared with suspensions (such as sterile injection solutions or oily solutions). Sterile injection preparations can also be used in diluents or solvents of sterile injections or suspensions during innocuous injections, for example, in solutions of 1,3-butanediol. Acceptable carriers or solvents include mannitol, water, ringer solution, and isotonic sodium chloride solution. Besides, sterilized and fixed oils are used in prior arts as solvents or suspension media(for example, synthesized monoglycerides or diglycerides). Fatty acids (such as oleic acids or glyceride derivatives) and natural pharmaceutically acceptable oils (such as olive oil or castor oil, especially polyoxyethylated derivatives thereof) can be used in injectable preparations. The oil solutions or suspensions can also comprise long-chain alcohol diluents, dispersants, caboxylmethyl cellulose, or similar dispersants. Other commonly used surfactants like Tweens and Spans, or emulsifiers and bioavailability enhancers (usually used in manufacturing pharmaceutically acceptable alum solids, liquids or other dosage forms) can also be used for preparing purposes.

Compositions for oral administration can be any dosage form acceptable for oral administration, comprising, but not limited to, capsules, tablets, emulsions, water suspensions, dispersants, and solutions. In cases of tablets for oral administration purposes, the typical carriers include lactose and corn starch. A lubricant is often added, such as magnesium stearate. For oral administration with capsules, suitable diluents include lactose and corn starch. In cases of oral administration of water dispersants or emulsions, active ingredients could associate with emulsions or suspensions to suspend or disperse in the oil phase. Depending on needs, certain sweeteners, flavoring agents, or coloring agents can be added.

A nasal aerosol or inhalation composition can be prepared according to techniques well-known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art. Compositions containing fusion proteins can also be administered in the form of suppositories for rectal administration.

The carriers of the pharmaceutical composition must be "acceptable", i.e. compatible to active ingredients in the formulation (preferably, capable of stabilizing the active ingredient) and not deleterious to the subject to be treated. Other examples of the carriers include colloidal silicon dioxide, magnesium stearate, cellose, sodium lauryl sulfate, and D&C yellow No.10.

The pharmaceutical composition of the fusion protein in the present invention preferably comprises an immune adjuvant. The immune adjuvant used is not limited and can be any conventional one used in vaccines known in the art, comprising Alumigel and oil emulsion, such as Freund's FCA or FIA or mannide mono-oleate emulsifier (ISA720 or ISA206, SEPPIC®, France), preferably ISA206.

Other objects, advantages, and novel features of the invention will become more apparent from the following detailed description when taken in conjunction with the accompanying drawings.

DETAILED DESCRIPTION OF THE PREFERRED EMBODIMENT

The feature of the present invention is based on a finding that, when most structure proteins in ORF5 and ORF6 were removed, leaving dozens of N-terminal amino acids of ORF5 and ORF6, by which constructing a fusion peptide chain PQGAB, and then inserting the peptide chain between PE and K3 sequence was possible, it was confirmed that the fusion protein PE-PQGAB-K3 had serum neutralization titers by mice and porcine immunization tests.

The following examples are proposed to explain the present invention, but not set forth as to limit the scope thereof.

EXAMPLE 1

PQGAB Fusion Peptide of PRRSV American Strain

The protein sequences of ORF5 and ORF6 of PRRSV were obtained from the National Center for Biotechnology Information (NCBI, USA) database. Based on aforementioned mechanisms of viral infections, the regions of PRRSV that have neutralization titers are located at the N-terminus of ORF5 and ORF6. That is, amino acid residues 2 to 26 of ORF6(SEQ ID NO.13) and amino acid resiues 31 to 63 of ORF5 structural proteins (SEQ ID NO.12). The amino acid sequence resulting from the fusion of the two peptides is illustrated below:

GSSLDDFCYDSTAPQKVLLAFSITYASNDSSSHLQLIYNLTLC
ELNGTDWLANKFDWA

The sequence of PRRSV-ORF6-2~26-ORF5-31~63 fusion peptide was the combination of (ORF6)-$G_2$SSLDDFCYDSTAPQKVLLAFSITY$_{26}$ (SEQ ID NO.13) and (ORF5)-$A_{31}$SNDSSSHLQLIYNLTLCELNGTDWLANKFDWA$_{63}$ (SEQ ID NO.12) peptides, wherein the fragment GSSLDDFC is designated "P", fragment YDSTAPQKVLLAFSITY "Q", fragment ASNDSSSHLQLIYNLTLC "A", and ELNGTDWLANKFDWA "B". Fragment PQ is a portion of ORF6, and Fragment AB is a portion of ORF5. G is the gap or bridge of PQ and AB ploypeptides. G can be the 27$^{th}$ animo acid of ORF6 or any polypeptide fragment of ORF6 from 27$^{th}$ to any linked codons. The position G can also be not added any amino acid within the polypeptides of PQ and AB.

Figure 1:
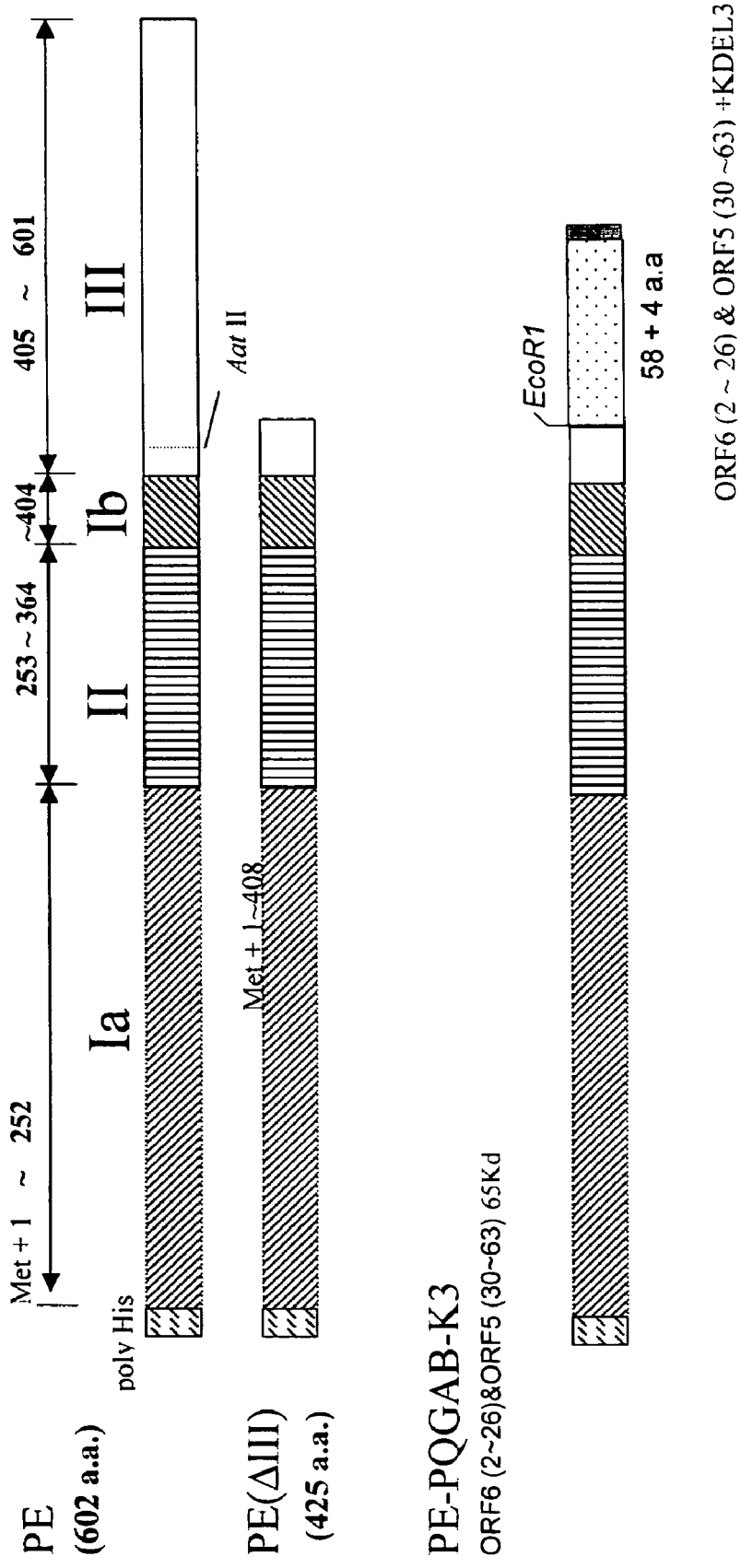
FIG. 1 is a schematic illustration of PE-PQGAB fusion protein of Example 1.
Figure 2:
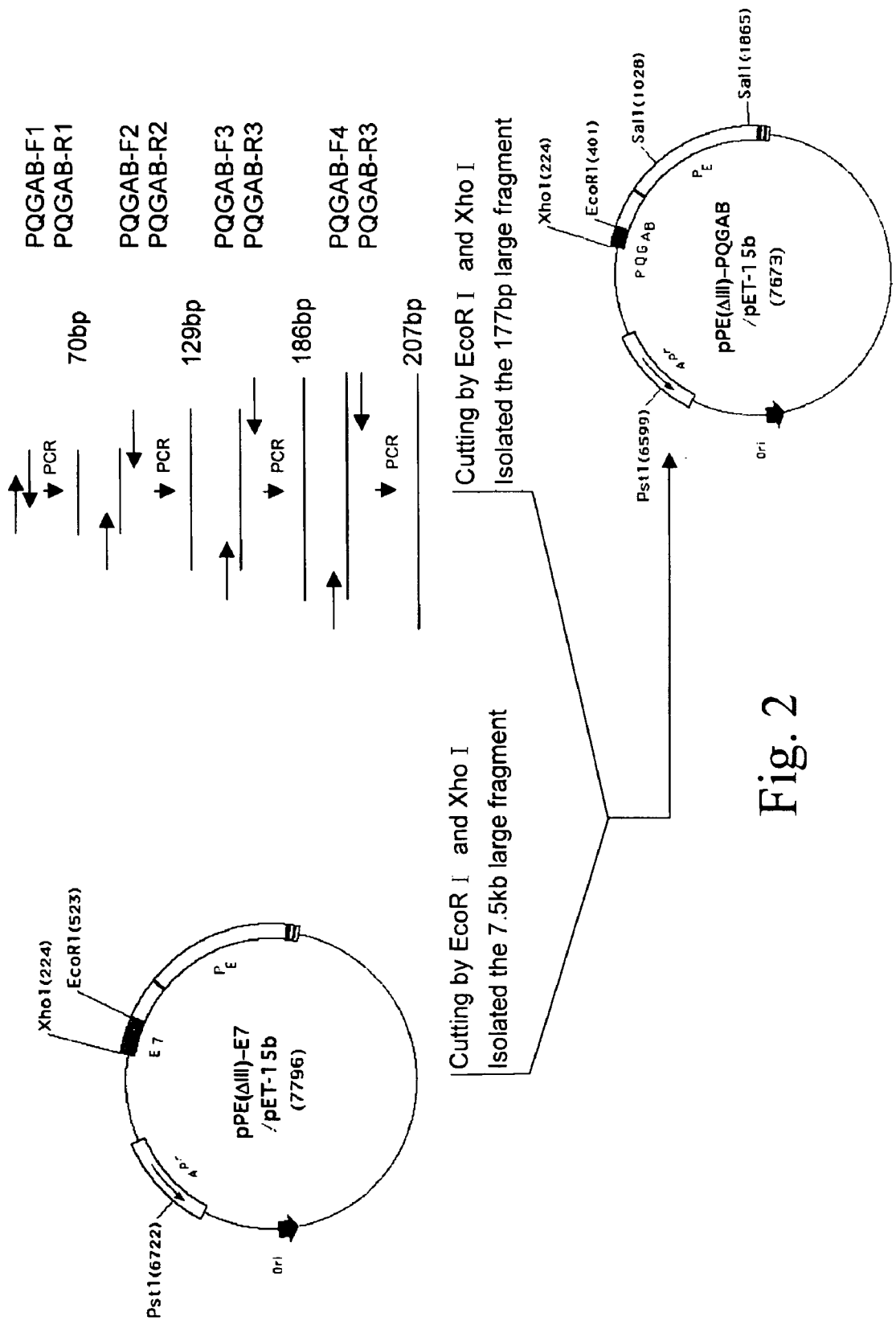
FIG. 2 is a flowchart of plasmid construction of PE(ΔIII)-PQGAB of Example 1.
Figure 2:
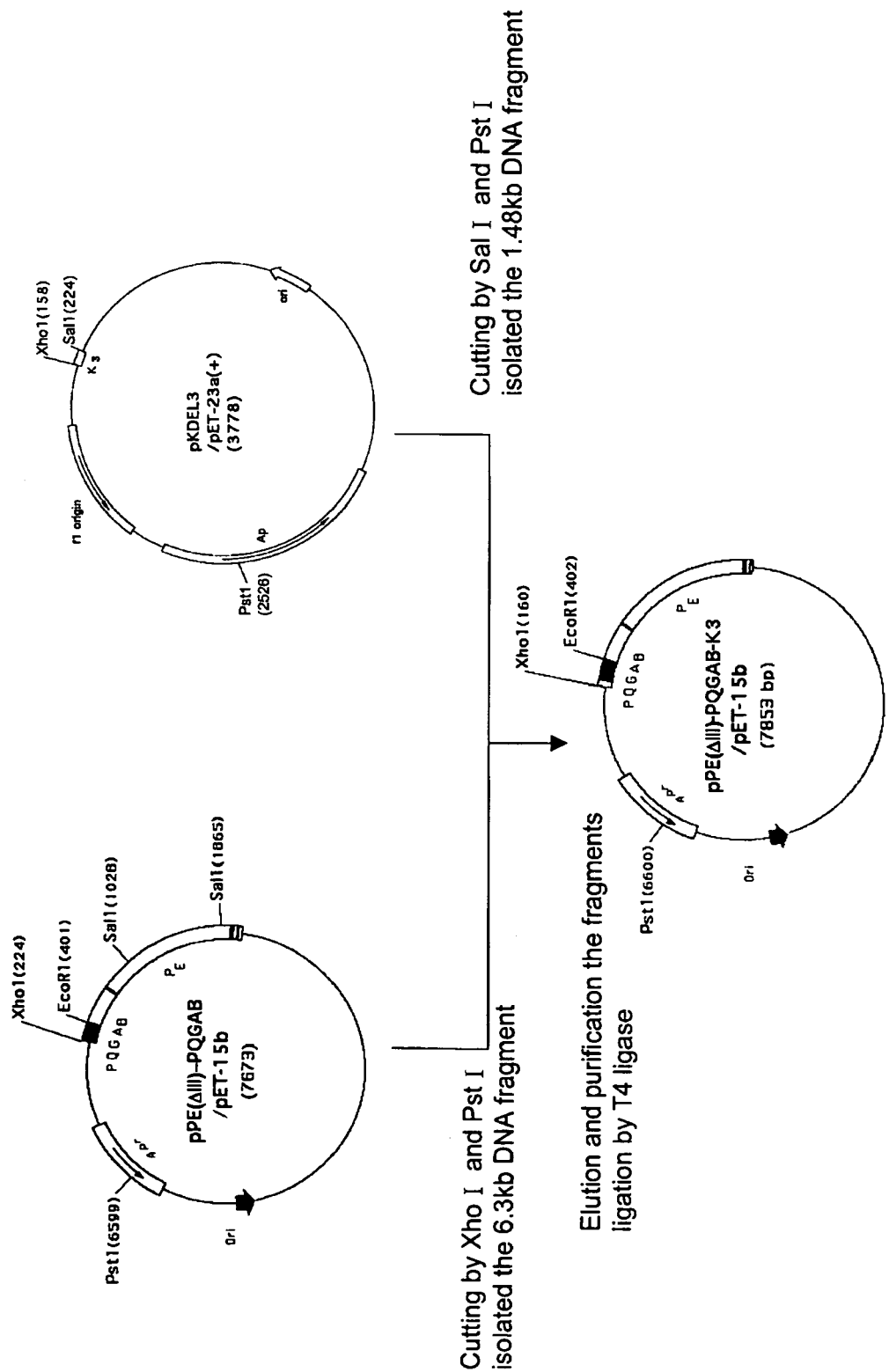

The example employs the PQGAB fusion peptide region to construct a key protein (epitope) capable of inducing neutralization titers and immune protection in order to obtain effects of inducing immune protection in vivo. The schematic illustration of PE-PQGAB-K3 fusion protein and the flowcharts of plasmids construction of PE(ΔIII)-PQGAB and PE(ΔIII)-PQGAB-K3 are shown in FIG. 1 and FIG. 2, respectively.

EXAMPLE 2

The preparation of nucleic sequence encoding PQGAB peptide is illustrated below. An amino acid corresponds to various sets of nucleotide triplets, so it is preferable to obtain corresponding nucleotide triplets from literature (such as http://www.kazusa.orjp/codon) that is suitable to be expressed in the *E. coli* system instead of the corresponding nucleotide triplets not easy to be recognized and expressed by *E. coli*. Likewise, if the sequence encoding PQGAB peptide is to be expressed in yeast systems, the appropriate nucleotide triplets for expression in yeast systems (such as *Saccharomycesor Pichia* spp.) are preferred.

A corresponding sequence with nucleotide triplets suitable to be expressed in *E. Coli* system was designated according to the amino acid sequence of PQGAB fusion protein. The 5' and 3' ends of the corresponding sequence were added by restriction sites for subsequent cloning. To improve efficiency of digestion and facilitate designing PCR primers, both ends of the sequence could be added to with nucleotide triplets with replicating bases, such as CCC, AAA, GGG, or TTT. The nucleic acid sequence encoding PQGAB fusion protein (SEQ ID NO:9) of the American strain of PRRSV is illustrated in SEQ ID NO:1.

There are totally 207 nucleotides in SEQ ID NO:1, in which the coding region is flanked by the restriction sites CATATG (NdeI), GAATTC (EcoR I) at 5' end, and CTCGAG (XhoI) at 3'. When it was cloned into a plasmid restriction enzyme sites, some of the nucleotide triplets were cut off, leaving 180-186 nucleotides ligated to the plasmid.

When the target nucleic acid sequence encoding PQGAB fusion protein was identified, the restriction map of the nucleic acid sequence was analyzed by DNA Strider before synthesis, and then each end of the target sequence was linked to restriction site sequences for subsequent cloning, in accordance with the restriction map. The synthesized product of the target sequence must be digested by certain restriction enzymes before cloning, so it is preferable that any restriction site susceptible to the enzymes used be avoided in the structural region of the sequence. If the restriction sites subjected to cloning enzymes exist in the structural region of the target sequence, the target sequence must be re-designated such that different codons of the same amino acids were used, to eliminate restriction sites that were identical for cloning in the structural region of the target sequence.

Subsequently, the method disclosed in Taiwan Patent No. 1-2289933 (also as U.S. patent publication no. 2004/02147617) is used to modify the corresponding nucleotides codons of wild type amino acids sequence such that the wild type protein was mass expressed in by *E. coli* system. The essence of modification is to modify wild type nucleic acid sequence such that the normally expressed amino acids were not affected, and expression in *E. coli* was kept effective. The modified nucleic acid sequence can be synthesized by PCR using a variety of primer pairs. The primers are numbered as shown in Table 1.

TABLE 1 the corresponding numbers of primers for PQGAB antigens of PRRSV American Strain

| Target antigen | Forward primer | Seq. ID No. | Reverse primer | Seq. ID No. |
|---|---|---|---|---|
| PQGAB-US | F1 | 2 | R1 | 6 |
| PQGAB-US | F2 | 3 | R2 | 7 |
| PQGAB-US | F3 | 4 | R3 | 8 |
| PQGAB-US | F4 | 5 | | |

The sequences of forward and reverse primers are shown as follows:

Forward primer F1 (SEQ ID No.2) corresponds to the nucleotides 79 -122 of SEQ ID NO: 1, namely

5'-GCT TTC TCC ATC ACC TAC GCT TCC AAC GAC TCC TCC TCC CAC CT-3';

Forward primer F2 (SEQ ID No:3) corresponds to the nucleotides 48-95 of SEQ ID No:1, namely

5'-C GAC TCC ACC GCT CCC CAG AAA GTT CTG CTG GCT TTC TCC ATC ACC TA-3';

Forward primer F3 (SEQ ID No:4) corresponds to the nucleotides 22-65 of SEQ ID No:1, namely

5'-GGT TCC TCC CTG GAC GAC TTC TGC TAC GAC TCC ACC GCT CCC CA-3';

Forward primer F4(SEQ ID No:5) corresponds to the nucleotides 1-40 of SEQ ID No:1, namely

5'-CCC AAA CCC CAT ATG GAA TTC GGT TCC TCC CTG GAC GAC T-3';

Reverse primer R1(SEQ ID No.6) corresponds to the nucleotides 148-106 of SEQ ID No.1, namely

5'-A CAG GGT CAG GTT GTA GAT CAG TTG CAG GTG GGA GGA GGA GTC-3';

Reverse primer R2(SEQ ID No.7) corresponds to the nucleotides 176-133 of SEQ ID No:1, namely

5'-GC CAG CCA GTC GGT ACC GTT CAG TTC GCA CAG GGT CAG GTT GTA-3';

Reverse primer R3(SEQ ID No.8) corresponds to the nucleotides 207-164 of SEQ ID No:1, namely

5'-TTT TTT CTC GAG AGC CCA GTC GAA TTT GTT AGC CAG CCA GTC GG-3';

wherein R1, R2 and R3 were reversely complementary sequences of a gene sequence.

The fragment synthesized with no DNA template was performed firstly. Forward primer F1 and reverse primer R1 were hybridized to each other, wherein 10-18 bases at 3' ends of each primer were designed complementary to each other, and the resultant complex was read and complemented by polymerase so as to obtain a double-stranded DNA template product.

After the first round of PCR, 0.01~4 μl of the PCR product was taken as the template DNA of the second round of PCR, adding therein the second primer pair, i.e. forward primer F2 and reverse primer R2, 0.01~4 μl each, in conjunction with needed dNTPs, reagents and Pfu polymerse, and the second round PCR was performed. Likewise, primer pair F3 and R3 were added therein and PCR was performed again; the procedures were repeated with primer pair F4 and R3, and thereby a modified PQGAB nucleic acid sequence having 207 bp was obtained.

Figure 3:
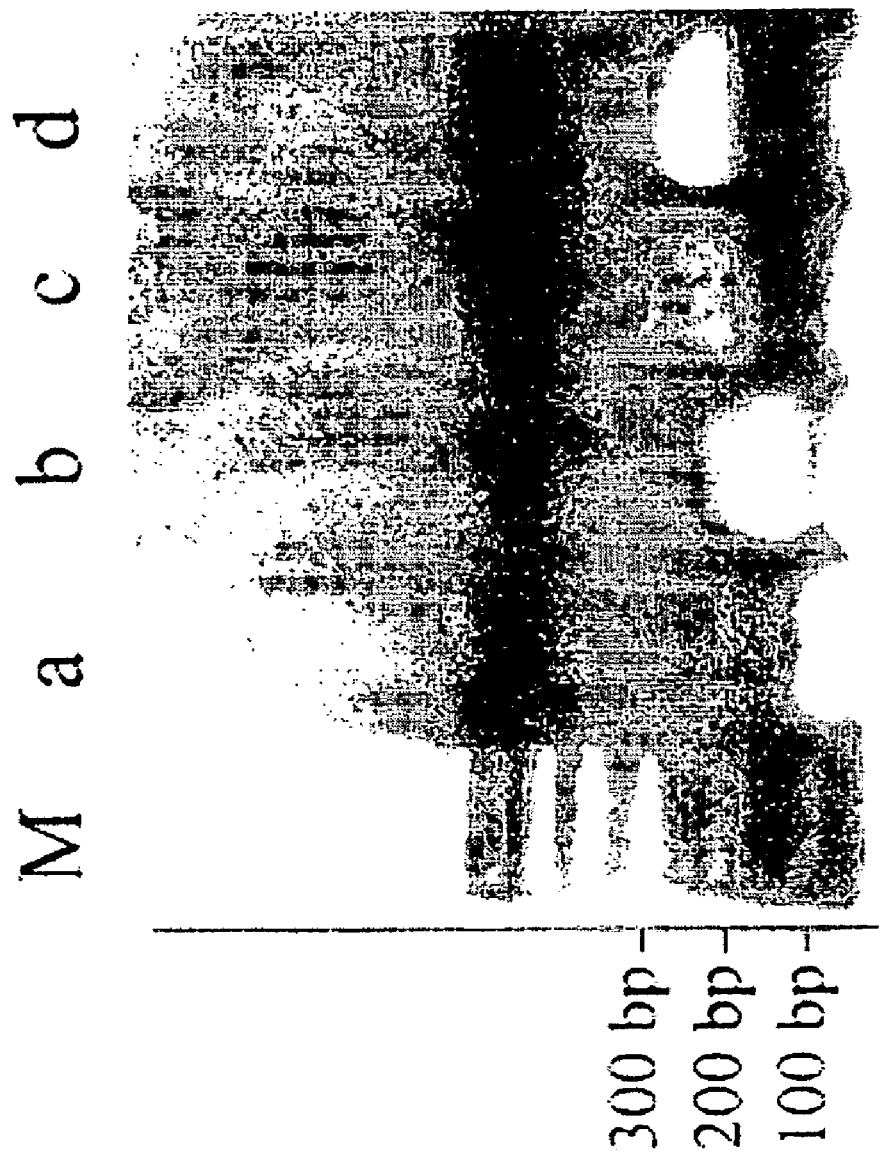
FIG. 3 is the electrophoresis diagram of the nucleic acid fragments synthesized according to Example 1, with four DNA fragments (a:70 bp, b:129 bp, c:186 bp, d:204 bp)

The synthesized nucleic acid fragments were subjected to electrophoresis and confirmed that they had the expected sizes. PQGAB-1(207 bp), as shown in FIG. 3; PQGAB generated 4 DNA fragments a, b, c, and d (a: 70 bp b: 129 bp c: 186 bp, d: 207 bp).

EXAMPLE 3

PQGAB Fragment of PRRSV European Strains

The design of the fusion protein in example 1 and 2 aimed at American strain PRRSV, but apart from American strain PRRSV, European strain and Australian strain is also very prevalent globally. Similarity of structural amino acids is not high, only 60-80%, so designs of other ORF5&ORF6 fusion proteins can be done in the same manner as example 1 and 2 to design and synthesize primers.

Taking PQGAB of the European strain of PRRSV as an example, the amino acid sequence of the fusion protein is shown in SEQ ID NO.10. It contains the amino acid residues from 1to 28of the ORF 6 (i.e., SEQ ID NO.15) structual proteins of the European strain of PRRSV.

After the sequence is confirmed, preparation of PRRSV European strain fusion proteins can be performed in the same manner as examples 1-2. The modified nucleic acid sequence can be synthesized by PCR using a variety of primer pairs. The primers are numbered as shown in Table 2.

TABLE 2 the corresponding numbers of primers for PQGAB antigens of PRRSV European Strain

| Target antigen | Forward primer | Seq. ID No. | Reverse primer | Seq. ID No. |
|---|---|---|---|---|
| PQGAB-EP | F1 | 16 | R1 | 20 |
| PQGAB-EP | F2 | 17 | R2 | 21 |
| PQGAB-EP | F3 | 18 | R3 | 22 |
| PQGAB-EP | F4 | 19 | R4 | 23 |

The target nucleic acid sequence encoding PQGAB-EP fusion protein can be synthesized with those primers shown above in vitro, by following the procedure described in example 2. To improve efficiency of digestion and facilitate designing PCR primers, both ends of the sequence could be added to with nucleotide triplets with replicating bases, such as CCC, AAA, GGG, or TTT. The nucleic acid sequence encoding PQGAB-EP fusion protein is illustrated in SEQ ID NO.11: in which the coding region is franked by the restrictions site GAATTC (EcoR I), CATATG (Nde I) and GACGTC (Sal I) at 5' end, and CTCGAG (Xho I) at 3'.

EXAMPLE 4

Construction of Plasmids Containing the Target Sequence

Taking the product from example 2 as illustration. The synthesized 207-bp DNA fragment was digested with EcoR1 and Xho1, linked to a E.coli plasmid containing a peptide sequence having functions of binding and translocation, and a carboxyl terminus peptide, and the resultant plasmid was pPE-PQGAB-K3.

Figure 4:
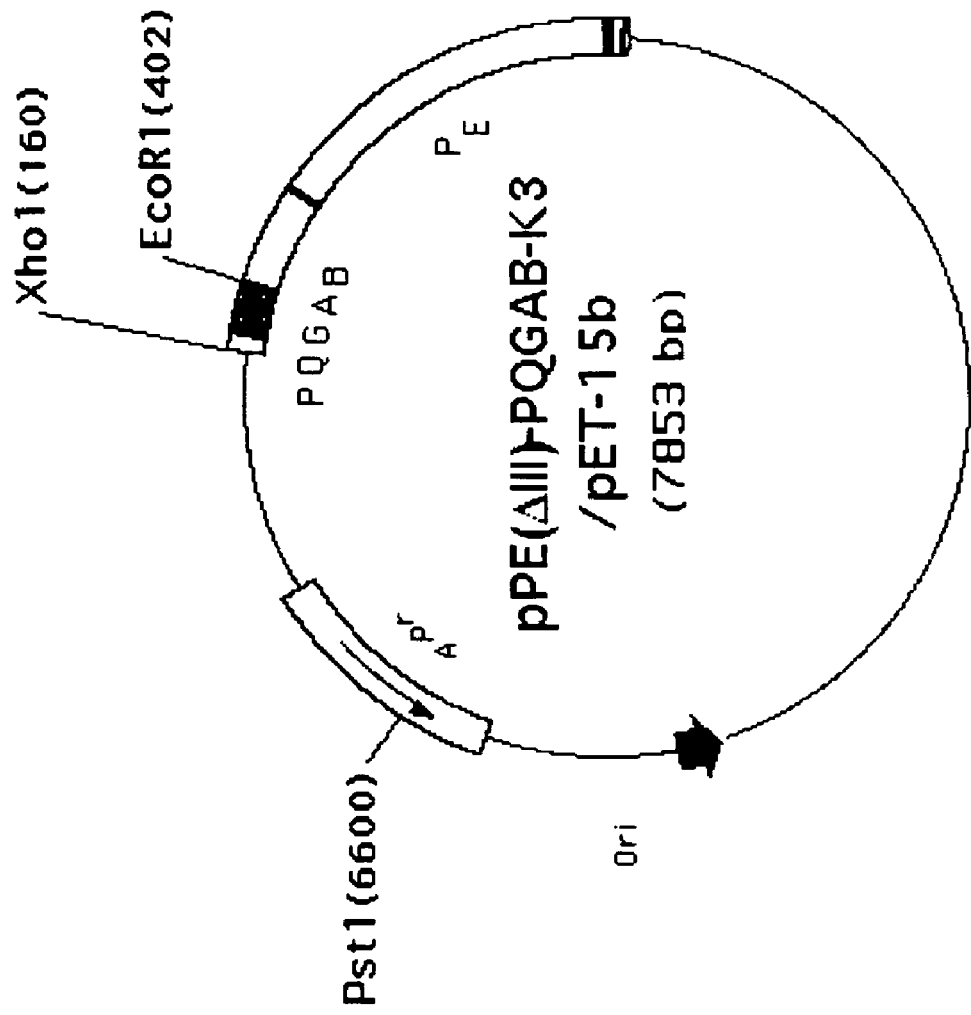
FIG. 4 is the plasmid map of PE(ΔIII)-PQGAB.

The pET15 plasmid having a T7 promoter and an antibiotic resistance(ampicillin) marker constructed therein can express the fusion protein of PRRSV PQGAB fragment and detoxified *Pseudomonas exotoxin* (*Pseudomonas exotoxin* A without domain III). The vector map is shown in FIG. 4.

Finally, the above-mentioned plasmid was transformed into bacterial strains or cells capable of expressing the fusion proteins.

EXAMPLE 5

Expression and Analysis of the Target Protein

Bacterial strains confirmed having the above mentioned plasmid contained both the plasmid and PQGAB gene in 90% of the population. The strains were prepared as glycerol stocks in 2-ml aliquots and stored at −70° C. In a sterile environment, 2 ml of the stored stocks was inoculated in an autoclaved 500 ml flask containing 200 ml LB (+500 µg/ml Amp), shaken in a rotary incubator at 37° C., 150 rpm for 10~12 hours, and a culture was obtained. The liquid was cultured until OD600 reached 1.0±0.4.

In a sterile environment, 50 ml culture liquid was inoculated in each of eight 3000-ml flasks containing 1250 ml LB (+500 µg/ml Amp +50 ml 10% Glucose), shaken at 37° C., 150 rpm for 2~3 hours until OD 600 reached 0.3±0.1, 50 ppm IPTG was added, the culture was shaken again at 37° C., 150 rpm for 2 hours such that protein production was accomplished.

Figure 5:
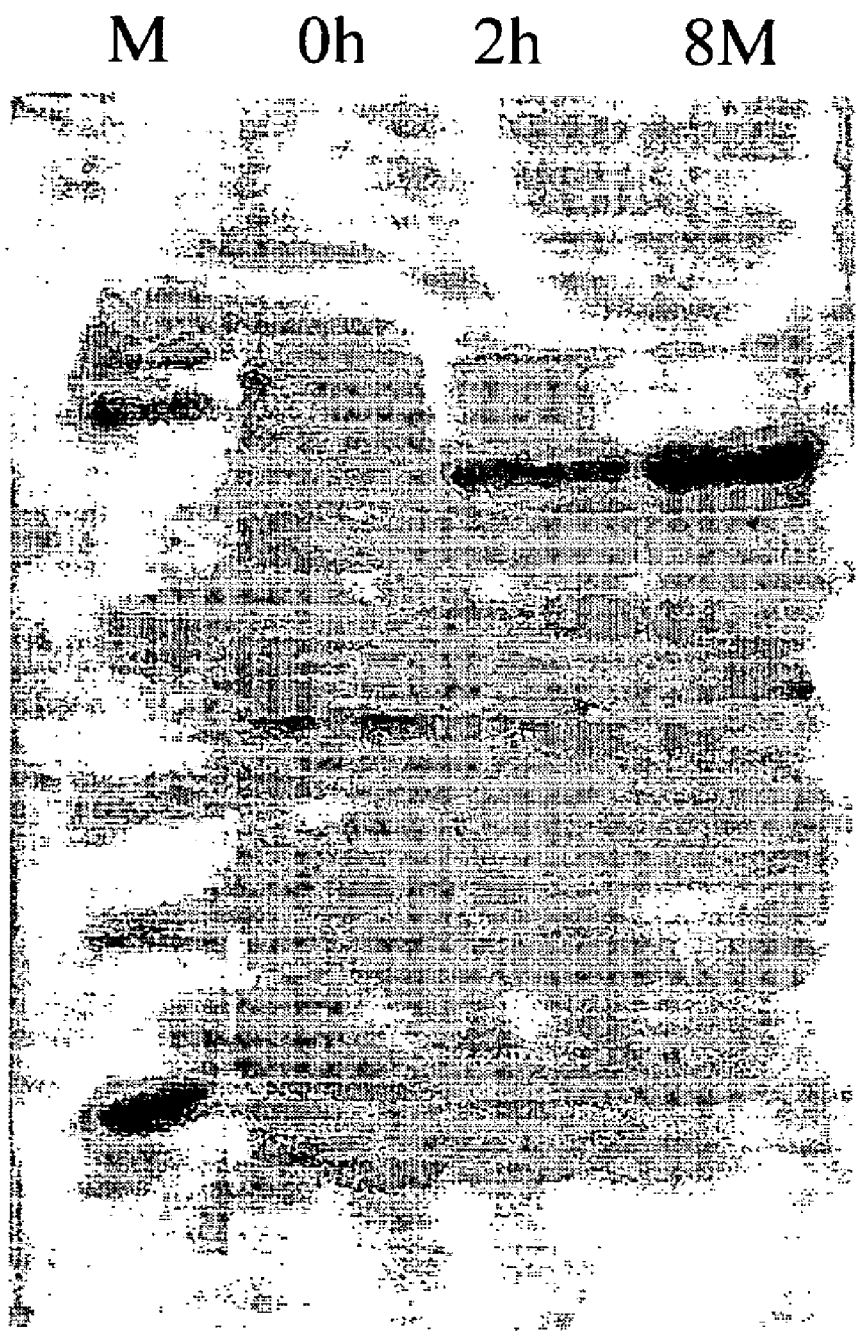
FIG. 5 is the result of proteins induced in *E. coli* Host-vector system and extracted from inclusion bodies by 8M urea extraction. lane 0h, 2h: the total lysis samples at 0 hr and 2 hr after IPTG induction of *E. coli* with pPE-PQGAB-K3; and lane 8M: 8M urea protein extraction of PE-PQGAB-K3.

Then PE-PQGAB-K3 contained in inclusion bodies was dissolved by 8M urea extraction method, the extracted PE-PQGAB-K3 proteins are shown in FIG. 5. 300~400 mg antigen could be obtained from a 10-liter lot of the culture liquid. Obtained antigen was analyzed with Western blot, coomasie blue staining and SDS-PAGE electrophoresis, the density of the bands was measured by densitometer to quantify proteins contained in antigen solutions. 0.2±0.02 mg of the proteins were used as the main ingredient of a low-dosage injection in order to proceed immunization and virus-challenging.

EXAMPLE 6

Immunization and Virus-Challenging in Pigs

In an SPF farm, pigs were grouped randomly into 3 groups, each having five pigs. Each group was bred in an isolation room equipped with air conditioning and circulation instruments. For pigs of PE-PQGAB-K3 immunization group aged 14 to 28 days, 2 ml vaccine containing 1 ml PE-PQGAB-K3 (containing 200 µg proteins/injection) and emulsified in 1 ml ISA206 (SEPPIC®, France) was injected intramuscularly, and the procedure of immunization was performed twice. The immunization group GP5&M was immunized with PE-ORF5-K3 及PE-ORF6-K3(containing 200 µg proteins/injection), respectively. The control group was bred without immunization.

Two weeks after the last inoculation, 100 mg ketamine solution was administered intramuscularly to tranquilize the pigs, then 1 ml 2% Lidocaine was dropped in the nasal cavities of the pigs to inhibit coughing reflex actions, and then the virus was inoculated in pigs nasally. Five pigs of each group were inoculated with 1 ml MD-1 strain PRRSV cultures having a $1 \times 10^7$ TCID$_{50}$/ml dosage.

14 days after inoculation, the pigs were sacrificed to proceed with complete autopsy. Lung or liver samples were collected (from both parts of the head lobe central part and auxiliary part of caudate lobe) and fixed by 10% neutral buffered formaldehyde for subsequent tissue pathology examination. The examination was conducted in a blind fashion and evaluated on the basis of interstitial pneumonitis severity (Opriessnig T, P. G. Halbur, et al., Journal of Virology, 76(2002):11837-11844, and Halbur, P. G., P. S. Paul, et al., 1996. J. Vet. Diagn. Investig. 8:11-20) in a scale from 0 to 6, wherein the severity increases with the number.

Experimental Results

Two weeks post second immunization, leukocytes from porcine blood were tested for PRRSV. The results indicated that viremia did not occur in any pig before PRRSV inoculating. The leukocyte samples were tested with RT-PCR at 3, 7, and 14 days post virus inoculating, respectively, and the results are shown in Table 3.

TABLE 3

PRRSV viremia occurrence in pigs post PRRSV inoculating

| Day | Control | PE-PQGAB-K3 | PE-ORF5-K3 PE-ORF6-K3 |
|---|---|---|---|
| 3 | 3/5 | 3/5 | 2/5 |
| 7 | 3/4 (death1*) | 2/5 | 2/4 (death2*) |
| 14 | 3/4 (death1*) | 2/5 | 2/4 (death2*) |

*identified with PRRSV viremia by RT-PCR before death

All pigs, including those that had been sacrificed and the surviving after the two-week study, were dissected. Macroscopic examinations indicated that the lungs from virus-inoculated pigs of ORF5&ORF6 vaccine group and the control group showed more extensive lesions and severe interstitial pneumonitis, whereas the PE-PQGAB-K3 vaccine group of the present invention did not show as extensive lesions and severe interstitial pneumonitis. As shown in Table 4, the PE-PQGAB-K3 vaccine group of the present invention showed less severity in terms of interstitial pneumonitis than the control group and ORF5&ORF6 vaccine group.

TABLE 4 comparisons of macroscopic lung lesions induced by PRRSV, 14 days post PRRSV inoculating

| Pig No. | Control group Lesion index | PE-PQGAB-K3 vaccine group Lesion index | PE-ORF5-K3, PE-ORF6-K3 vaccine group Lesion index |
|---|---|---|---|
| 1 | 6* | 5 | 6 |
| 2 | 6 | 3 | 5 |
| 3 | 6 | 4 | 6 |
| 4 | 6 | 4 | 6 |
| 5 | 5 | 3 | 6 |
| Average | 5.75 ± 0.50 | 3.80 ± 0.84 | 5.80 ± 0.45 |

*interstitial pneumonitis lesion index

TABLE 5 macroscopic lung lesion indexes exhibited by the PE-PQGAB-K3 vaccine group are significantly lower than control group and ORF5&ORF6 vaccine group in view of biostatistics.

| Group | Number of individuals | Total | Average | Variance |
|---|---|---|---|---|
| Control group | 5 | 29 | 5.8 | 0.2 |
| PE-PQGAB-K3 group | 5 | 19 | 3.8 | 0.7 |
| PE-ORF5&ORF6-K3 group | 5 | 29 | 5.8 | 0.2 |

ANOVA

| Variation source | SS | Degree of freedom | MS | F | P-value | Critical value |
|---|---|---|---|---|---|---|
| Inter-group | 13.33333 | 2 | 6.666667 | 18.18182 | 0.000233 | 3.885294 |
| Intra-group | 4.4 | 12 | 0.366667 | | | |
| total | 17.73333 | 14 | | | | |

The above experiments clearly indicate that PE-PQGAB-K3 of the present invention not only can effectively protect pigs from PRRSV infections, but also cause slighter interstitial pneumonitis than other vaccines (such as PE-ORF5-K3, PE-ORF6-K3).

The antibody titers variation in immunized pigs are shown in table 6. The A group has good IgG ELISA titers, but the IFA and NT titers are less than that of C group. Also, from table 5, it indicates that PRRSV ORF5 or ORF6 have an antigen-specific allergy effect after immunization and virus challenged. Manifestly, it is difficult to use them as PRRS vaccine antigens.

TABLE 6

| | Serum titers | | | |
|---|---|---|---|---|
| | coating antigen | | | |
| Group | PE(Δ III) IgG-ELISA titers (S/BK) | PQGAB | IFA titers | NT titers* |
| A PE-ABCF-K3 PE-PQGF-K3 | 12 | 80 | 8-16 | 8-16 |
| B Negative CTL | 1 | 1 | <8 | <8 |
| C PE-PQG1AB-K3 | 17 | 30 | 32-64 | 16-64 |

*The neutralization titer is determined by the inhibition growth and proliferation of PRRSV under serial dilution sample added in MAC-10A cells culture system.

Although the present invention has been explained in relation to its preferred embodiment, it is to be understood that many other possible modifications and variations can be made without departing from the scope of the invention as hereinafter claimed.

SEQUENCE LISTING

<160> NUMBER OF SEQ ID NOS: 23

<210> SEQ ID NO 1
<211> LENGTH: 207
<212> TYPE: DNA
<213> ORGANISM: Porcine reproductive and respiratory syndrome virus

<400> SEQUENCE: 1

```
cccaaacccc atatggaatt cggttcctcc ctggacgact tctgctacga ctccaccgct      60
ccccagaaag ttctgctggc tttctccatc acctacgctt ccaacgactc ctcctcccac     120
ctgcaactga tctacaacct gaccctgtgc gaactgaacg gtaccgactg gctggctaac     180
aaattcgact gggctctcga gaaaaaa                                         207
```

<210> SEQ ID NO 2
<211> LENGTH: 44
<212> TYPE: DNA
<213> ORGANISM: Artificial
<220> FEATURE:
<223> OTHER INFORMATION: Foward primer for PQGAB-US.

<400> SEQUENCE: 2

```
gctttctcca tcacctacgc ttccaacgac tcctcctccc acct                       44
```

<210> SEQ ID NO 3
<211> LENGTH: 48
<212> TYPE: DNA
<213> ORGANISM: Artificial
<220> FEATURE:
<223> OTHER INFORMATION: Foward primer for PQGAB-US.

<400> SEQUENCE: 3

```
cgactccacc gctccccaga aagttctgct ggctttctcc atcaccta                   48
```

<210> SEQ ID NO 4
<211> LENGTH: 44
<212> TYPE: DNA
<213> ORGANISM: Artificial
<220> FEATURE:
<223> OTHER INFORMATION: Foward primer for PQGAB-US.

<400> SEQUENCE: 4

```
ggttcctccc tggacgactt ctgctacgac tccaccgctc ccca                       44
```

<210> SEQ ID NO 5
<211> LENGTH: 44
<212> TYPE: DNA
<213> ORGANISM: Artificial
<220> FEATURE:
<223> OTHER INFORMATION: Foward primer for PQGAB-US

<400> SEQUENCE: 5

```
ggttcctccc tggacgactt ctgctacgac tccaccgctc ccca                       44
```

<210> SEQ ID NO 6
<211> LENGTH: 43
<212> TYPE: DNA
<213> ORGANISM: Artificial
<220> FEATURE:
<223> OTHER INFORMATION: Reverse primer for PQGAB-US.

<400> SEQUENCE: 6

```
acagggtcag gttgtagatc agttgcaggt gggaggagga gtc                        43
```

<210> SEQ ID NO 7
<211> LENGTH: 44
<212> TYPE: DNA
<213> ORGANISM: Artificial
<220> FEATURE:
<223> OTHER INFORMATION: Reverse primer for PQGAB-US.

<400> SEQUENCE: 7
gccagccagt cggtaccgtt cagttcgcac agggtcaggt tgta          44

<210> SEQ ID NO 8
<211> LENGTH: 44
<212> TYPE: DNA
<213> ORGANISM: Artificial
<220> FEATURE:
<223> OTHER INFORMATION: Reverse primer for PQGAB-US.

<400> SEQUENCE: 8 tttttctcg agagcccagt cgaatttgtt agccagccag tcgg          44

<210> SEQ ID NO 9
<211> LENGTH: 207
<212> TYPE: PRT
<213> ORGANISM: Porcine reproductive and respiratory syndrome virus

<400> SEQUENCE: 9

Cys Cys Cys Ala Ala Ala Cys Cys Cys Ala Thr Ala Thr Gly Gly
1               5                   10                  15

Ala Ala Thr Thr Cys Gly Gly Thr Cys Cys Thr Cys Cys Cys Thr
                20                  25                  30

Gly Gly Ala Cys Gly Ala Cys Thr Thr Cys Thr Gly Cys Thr Ala Cys
            35                  40                  45

Gly Ala Cys Thr Cys Cys Ala Cys Cys Gly Cys Thr Cys Cys Cys Cys
        50                  55                  60

Ala Gly Ala Ala Ala Gly Thr Thr Cys Thr Gly Cys Thr Gly Gly Cys
65                  70                  75                  80

Thr Thr Thr Cys Thr Cys Cys Ala Thr Cys Ala Cys Cys Thr Ala Cys
                85                  90                  95

Gly Cys Thr Thr Cys Cys Ala Ala Cys Gly Ala Cys Thr Cys Cys Thr
            100                 105                 110

Cys Cys Thr Cys Cys Cys Ala Cys Cys Thr Gly Cys Ala Ala Cys Thr
        115                 120                 125

Gly Ala Thr Cys Thr Ala Cys Ala Ala Cys Cys Thr Gly Ala Cys Cys
    130                 135                 140

Cys Thr Gly Thr Gly Cys Gly Ala Ala Cys Thr Gly Ala Ala Cys Gly
145                 150                 155                 160

Gly Thr Ala Cys Cys Gly Ala Cys Thr Gly Gly Cys Thr Gly Gly Cys
                165                 170                 175

Thr Ala Ala Cys Ala Ala Ala Thr Thr Cys Gly Ala Cys Thr Gly Gly
            180                 185                 190

Gly Cys Thr Cys Thr Cys Gly Ala Gly Ala Ala Ala Ala Ala
        195                 200                 205

<210> SEQ ID NO 10
<211> LENGTH: 219
<212> TYPE: PRT
<213> ORGANISM: Porcine reproductive and respiratory syndrome virus

<400> SEQUENCE: 10

-continued

Cys Cys Cys Gly Ala Ala Thr Thr Cys Ala Thr Ala Thr Gly Gly
1               5                   10                  15

Thr Cys Gly Ala Cys Ala Thr Gly Gly Thr Thr Cys Thr Cys Thr
                20                  25                  30

Cys Gly Ala Cys Gly Ala Cys Thr Thr Thr Gly Thr Ala Ala Cys
                35                  40                  45

Gly Ala Cys Thr Cys Thr Ala Cys Cys Gly Cys Thr Gly Cys Thr
        50                  55                  60

Cys Ala Gly Ala Ala Cys Thr Gly Gly Thr Thr Cys Thr Gly Gly
65                  70                  75                  80

Thr Thr Thr Thr Thr Cys Thr Ala Thr Cys Ala Cys Cys Thr Ala
                85                  90                  95

Cys Ala Cys Cys Cys Ala Ala Thr Cys Thr Thr Thr Gly Thr Thr
                100                 105                 110

Gly Cys Thr Gly Gly Thr Gly Gly Thr Cys Thr Thr Cys Thr Thr
        115                 120                 125

Cys Thr Ala Cys Cys Ala Gly Thr Ala Cys Ala Thr Cys Thr Ala
        130                 135                 140

Cys Ala Ala Cys Thr Cys Ala Cys Cys Ala Thr Cys Thr Gly Thr
        145                 150                 155                 160

Gly Ala Ala Cys Thr Cys Ala Ala Cys Gly Gly Thr Ala Cys Cys
                165                 170                 175

Gly Ala Cys Thr Gly Gly Cys Thr Gly Thr Cys Thr Ala Ala Cys
            180                 185                 190

Cys Ala Cys Thr Thr Thr Gly Ala Cys Thr Gly Gly Gly Cys Thr
            195                 200                 205

Cys Thr Cys Gly Ala Gly Ala Ala Ala Ala Ala
            210                 215

<210> SEQ ID NO 11
<211> LENGTH: 219
<212> TYPE: DNA
<213> ORGANISM: Porcine reproductive and respiratory syndrome virus

<400> SEQUENCE: 11
cccgaattcc atatggtcga catgggttct ctcgacgact tttgtaacga ctctaccgct      60
gctcagaaac tggttctggc tttttctatc acctacaccc caatctttgt tgctggtggt     120
tcttcttcta cctaccagta catctacaac ctcaccatct gtgaactcaa cggtaccgac     180
tggctgtcta accactttga ctgggctctc gagaaaaaa                            219

<210> SEQ ID NO 12
<211> LENGTH: 33
<212> TYPE: PRT
<213> ORGANISM: Porcine reproductive and respiratory syndrome virus

<400> SEQUENCE: 12

Ala Ser Asn Asp Ser Ser Ser His Leu Gln Leu Ile Tyr Asn Leu Thr
1               5                   10                  15

Leu Cys Glu Leu Asn Gly Thr Asp Trp Leu Ala Asn Lys Phe Asp Trp
                20                  25                  30

Ala

<210> SEQ ID NO 13
<211> LENGTH: 25
<212> TYPE: PRT

-continued

<213> ORGANISM: Porcine reproductive and respiratory syndrome virus

<400> SEQUENCE: 13

Gly Ser Ser Leu Asp Asp Phe Cys Tyr Asp Ser Thr Ala Pro Gln Lys
1               5                   10                  15

Val Leu Leu Ala Phe Ser Ile Thr Tyr
            20                  25

<210> SEQ ID NO 14
<211> LENGTH: 28
<212> TYPE: PRT
<213> ORGANISM: Porcine reproductive and respiratory syndrome virus

<400> SEQUENCE: 14

Met Gly Ser Leu Asp Asp Phe Cys Asn Asp Ser Thr Ala Ala Gln Lys
1               5                   10                  15

Leu Val Leu Ala Phe Ser Ile Thr Tyr Thr Pro Ile
            20                  25

<210> SEQ ID NO 15
<211> LENGTH: 34
<212> TYPE: PRT
<213> ORGANISM: Porcine reproductive and respiratory syndrome virus

<400> SEQUENCE: 15

Phe Val Ala Gly Gly Ser Ser Thr Tyr Gln Tyr Ile Tyr Asn Leu
1               5                   10                  15

Thr Ile Cys Glu Leu Asn Gly Thr Asp Trp Leu Ser Asn His Phe Asp
            20                  25                  30

Trp Ala

<210> SEQ ID NO 16
<211> LENGTH: 42
<212> TYPE: DNA
<213> ORGANISM: Artificial
<220> FEATURE:
<223> OTHER INFORMATION: Foward primer for PQGAB-EP.

<400> SEQUENCE: 16
ctggcttttt ctatcaccta cacccccaatc tttgttgctg gt                            42

<210> SEQ ID NO 17
<211> LENGTH: 41
<212> TYPE: DNA
<213> ORGANISM: Artificial
<220> FEATURE:
<223> OTHER INFORMATION: Foward primer for PQGAB-EP.

<400> SEQUENCE: 17
gactctaccg ctgctcagaa actggttctg gcttttttcta t                             41

<210> SEQ ID NO 18
<211> LENGTH: 39
<212> TYPE: DNA
<213> ORGANISM: Artificial
<220> FEATURE:
<223> OTHER INFORMATION: Foward primer for PQGAB-EP.

<400> SEQUENCE: 18
ggttctctcg acgactttg taacgactct accgctgct                                  39

<210> SEQ ID NO 19
<211> LENGTH: 38

-continued

```
<212> TYPE: DNA
<213> ORGANISM: Artificial
<220> FEATURE:
<223> OTHER INFORMATION: Foward primer for PQGAB-EP.

<400> SEQUENCE: 19
cccgaattcc atatggtcga catgggttct ctcgacga                    38

<210> SEQ ID NO 20
<211> LENGTH: 42
<212> TYPE: DNA
<213> ORGANISM: Artificial
<220> FEATURE:
<223> OTHER INFORMATION: Reverse primer for PQGAB-EP.

<400> SEQUENCE: 20
gatgtactgg taggtagaag aagaaccacc agcaacaaag at               42

<210> SEQ ID NO 21
<211> LENGTH: 42
<212> TYPE: DNA
<213> ORGANISM: Artificial
<220> FEATURE:
<223> OTHER INFORMATION: Reverse primer for PQGAB-EP.

<400> SEQUENCE: 21
gttgagttca cagatggtga ggttgtagat gtactggtag gt               42

<210> SEQ ID NO 22
<211> LENGTH: 39
<212> TYPE: DNA
<213> ORGANISM: Artificial
<220> FEATURE:
<223> OTHER INFORMATION: Reverse primer for PQGAB-EP.

<400> SEQUENCE: 22
gtggttagac agccagtcgg taccgttgag ttcacagat                   39

<210> SEQ ID NO 23
<211> LENGTH: 38
<212> TYPE: DNA
<213> ORGANISM: Artificial
<220> FEATURE:
<223> OTHER INFORMATION: Reverse primer for PQGAB-EP.

<400> SEQUENCE: 23 tttttctcg agagcccagt caaagtggtt agacagcc                     38
```

What is claimed is:

1. A fusion protein of porcine reproductive and respiratory syndrome virus (PRRSV) comprising:
   a. a Pseudomonas Exotoxin A (PE) peptide comprising a binding domain and a translocating domain;
   b. a N-terminal portion of PRRSV ORF6 protein;
   c. a N-terminal portion of PRRSV ORF5 protein; and
   d. a carboxyl terminal domain comprising an amino acid sequence KDEL, wherein the PE peptide is located at the N-terminus of the fusion protein, and the N-terminal portion of PRRSV ORF5 protein is located between the N-terminal portion of PRRSV ORF6 protein and the carboxyl terminal domain.

2. The fusion protein of claim 1, wherein the N-terminal portion of PRRSV ORF6 protein comprises an amino acid sequence set forth by SEQ ID NO: 13 or SEQ ID NO: 14.

3. The fusion protein of claim 1, wherein the N-rerminalportion of PRRSV ORF5 comprises an amino acid sequence set forth by SEQ ID NO: 12 or SEQ ID NO: 15.

4. The fusion protein of claim 3, wherein the N-terminal portion of PRRSV ORF6 protein comprises an amino acid sequence set forth by SEQ ID NO: 13 or SEQ ID NO: 14.

5. A fusion protein of porcine reproductive and respiratory syndrome virus (PRRSV) comprising:
   a. a Pseudomonas Exotoxin A (PE) peptide comprising a binding domain and a translocating domain:
   b. a peptide fragment containing PRRSV ORF6 protein that is devoid of the C-terminal portion:
   c. a peptide fragment containing PRRSV ORF5 protein that is devoid of the C-terminal portion: and
   d. a carboxyl terminal domain comprising an amino acid secuuence KDEL, wherein the PE peptide is located at the N-terminus of the fusion protein, and the peptide fragment containing PRRSV ORF5 Protein is located between the peptide fragment containing PRRSV ORF6 protein and the carboxyl terminal domain.

6. The fusion protein of claim 5, wherein the carboxyl terminal domain comprises an amino acid sequence KDEL-RDELKDEL.

7. The fusion protein of claim 5, wherein the peptide fragment containing PRRSV ORF6 protein and the peptide fragment containing PRRSV ORF5 protein each comprise at least one neutralization epitope.

8. The fusion protein of claim 1, wherein the N-terminal portion of PRRSV ORF6 protein and the N-terminal portion of PRRSV ORF5 protein each comprise at least one neutralization epitope.

9. The fusion protein of claim 1, wherein the PRRSV is at least one selected from the group consisting of an American strain, an European strain, and an Australian strain.

10. The fusion protein of claim 1, wherein the carboxyl terminal comprises an amino acid sequence KDEL-RDELKDEL.

11. A vaccine composition for treating and/or preventing PRRS, comprising an effective amount of the fusion protein of claim 1 and a pharmaceutically acceptable carrier.

12. A vaccine composition for treating and/or preventing PRRS, comprising an effective amount of the fusion protein of claim 2 and a pharmaceutically acceptable carrier.

13. A vaccine composition for treating and/or preventing PRRS, comprisg an effective amount of the fusion protein of claim 3 and a pharmaceutically acceptable carrier.

14. A vaccine composition for treating and/or preventing PRRS, comprising an effective amount of the fusion protein of claim 4 and a pharmaceutically acceptable carrier.

15. A vaccine composition for treating and/or preventing PRRS, comprising an effective amount of the fusion protein of claim 5 and a pharmaceutically acceptable carrier.

16. A vaccine composition for treating and/or preventing PRRS, comprising an effective amount of the fusion protein of claim 6 and a pharmaceutically acceptable carrier.

17. A vaccine composition for treating and/or preventing PRRS, comprising an effective amount of the fusion protein of claim 7 and a pharmaceutically acceptable carrier.

18. A vaccine composition for treating and/or preventing PRRS, comprising an effective amount of the fusion protein of claim 8 and a pharmaceutically acceptable carrier.

19. A vaccine composition for treating and/or preventing PRRS, comprising an effective amount of the fusion protein of claim 9 and a pharmaceutically acceptable carrier.

20. A vaccine composition for treating and/or preventing PRRS, comprising an effective amount of the fusion protein of claim 10 and a pharmaceutically acceptable carrier.

* * * * *

UNITED STATES PATENT AND TRADEMARK OFFICE
CERTIFICATE OF CORRECTION

PATENT NO. : 7,465,455 B2 Page 1 of 1
APPLICATION NO. : 11/480387
DATED : December 16, 2008
INVENTOR(S) : Hsiu-Kang Chang and Chao-Wei Liao It is certified that error appears in the above-identified patent and that said Letters Patent is hereby corrected as shown below:

Column 2, Line 16, delete "containing" and substitute --containing KDEL-RDEL-KDEL(K3)--

Column 2, Line 23, delete "containing" and substitute --containing KDEL-RDEL-KDEL(K3)--

Column 7, Line 16, delete "28of the ORF 6" and substitute --28 of the ORF6 (i.e., SEQ ID NO: 14) and the amino acid residues from 31 to 64 of the ORF5--

Column 7, Line 46, delete "3" and substitute --3' end--

Signed and Sealed this

Fifteenth Day of June, 2010

David J. Kappos
*Director of the United States Patent and Trademark Office*

UNITED STATES PATENT AND TRADEMARK OFFICE
CERTIFICATE OF CORRECTION

PATENT NO. : 7,465,455 B2
APPLICATION NO. : 11/480387
DATED : December 16, 2008
INVENTOR(S) : Hsiu-Kang Chang and Chao-Wei Liao It is certified that error appears in the above-identified patent and that said Letters Patent is hereby corrected as shown below:

In the SEQUENCE LISTING, SEQ ID NOs: 9 and 10 should be replaced with the corrected SEQ ID NOs: 9 and 10 as shown below and on the attached sheets.

Col. 13, Line 45-57

```
<210>  9
<211>  58
<212>  PRT
<213>  Artificial sequence

<220>

<223>  fusion protein PQGAB of American strain PRRVS in Example 2

<400>  9

Gly Ser Ser Leu Asp Asp Phe Cys Tyr Asp Ser Thr Ala Pro Gln Lys
1               5                   10                  15

Val Leu Leu Ala Phe Ser Ile Thr Tyr Ala Ser Asn Asp Ser Ser Ser
            20                  25                  30

His Leu Gln Leu Ile Tyr Asn Leu Thr Leu Cys Glu Leu Asn Gly Thr
        35                  40                  45

Asp Trp Leu Ala Asn Lys Phe Asp Trp Ala
    50                  55
```

Signed and Sealed this

Ninth Day of November, 2010

David J. Kappos
*Director of the United States Patent and Trademark Office*

CERTIFICATE OF CORRECTION (continued)
U.S. Pat. No. 7,465,455 B2

Col. 13 & 15 Line 60-65 & Line 1-5

```
<210>  10
<211>  62
<212>  PRT
<213>  Artificial sequence

<220>

<223>  fusion protein PQGAB of European Strain PRRVS in Example 2

<400>  10

Met Gly Ser Leu Asp Asp Phe Cys Asn Asp Ser Thr Ala Ala Gln Lys
1               5                   10                  15

Leu Val Leu Ala Phe Ser Ile Thr Tyr Thr Pro Ile Phe Val Ala Gly
            20                  25                  30

Gly Ser Ser Ser Thr Tyr Gln Tyr Ile Tyr Asn Leu Thr Ile Cys Glu
            35                  40                  45

Leu Asn Gly Thr Asp Trp Leu Ser Asn His Phe Asp Trp Ala
    50                  55                  60
```